United States Patent
Miller et al.

(10) Patent No.: US 7,019,291 B2
(45) Date of Patent: Mar. 28, 2006

(54) NOX MONITOR USING DIFFERENTIAL MOBILITY SPECTROMETRY

(75) Inventors: Raanan A. Miller, Boston, MA (US); Erkinjon G. Nazarov, Lexington, MA (US); Muning Zhong, Worcester, MA (US)

(73) Assignee: Sionex Corporation, Waltham, MA (US)

( * ) Notice: Subject to any disclaimer, the term of this patent is extended or adjusted under 35 U.S.C. 154(b) by 47 days.

(21) Appl. No.: 10/684,332

(22) Filed: Oct. 10, 2003

(65) Prior Publication Data

US 2004/0136872 A1 Jul. 15, 2004

Related U.S. Application Data

(60) Provisional application No. 60/418,235, filed on Oct. 12, 2002.

(51) Int. Cl.
*A61B 5/08* (2006.01)
*G01J 3/44* (2006.01)

(52) U.S. Cl. .................. 250/292; 250/281; 250/288; 422/83; 422/84; 600/532; 356/303

(58) Field of Classification Search ............. 422/83–84; 600/532; 356/303; 250/281, 282, 284, 287, 250/289, 290, 291, 292

See application file for complete search history.

(56) References Cited

U.S. PATENT DOCUMENTS

| | | | |
|---|---|---|---|
| 2,615,135 A | 10/1952 | Glenn | |
| 3,511,986 A | 5/1970 | Llewellyn | |
| 3,619,605 A | 11/1971 | Cook et al. | |
| 3,621,240 A | 11/1971 | Cohen et al. | |
| 3,931,589 A | 1/1976 | Aisenberg et al. | |

(Continued)

FOREIGN PATENT DOCUMENTS

| | | |
|---|---|---|
| SU | 966583 | 10/1982 |
| SU | 1337934 A2 | 9/1987 |
| SU | 1627984 A2 | 7/1988 |
| SU | 1412447 A1 | 6/1998 |
| SU | 1485808 | 10/1998 |

(Continued)

OTHER PUBLICATIONS

"A Micromachined Field Driven Radio Frequency–Ion Mobility Spectrometer for Trace Level Chemical Detection," A Draper Laboratory Proposal Against the "Advanced Cross–Enterprise Technology Development for NASA Missions," Solicitation, NASA NRA 99–OSS–05.

Barnett, D.A. et al., "Isotope Separation Using High–Field Asymmetric Waveform Ion Mobility Spectrometry," Nuclear Instruments & Methods in Physics Research (2000), pp 179–185, 450(1).

Buryakov, I.A. et al., "Separation Ions According to Mobility in a Strong ac electric Field," Sov. Tech. Phs. Lett. (1991), pp 446–447, 17(6).

Buryakov, I.A. et al., Device and Method For Gas Electrophoresis, Chemical Analysis of Environment, edit. Prof. V.V. Malakhov, Novosibirsk; Nauka (1991), pp 113–127.

(Continued)

*Primary Examiner*—John R. Lee
*Assistant Examiner*—David A. Vanore
(74) *Attorney, Agent, or Firm*—Ropes & Gray LLP (57) ABSTRACT

System for detection and analysis of gas samples in fieldable real-time Differential Mobility Spectrometry (DMS) chemical sensor system which uses non-radioactive ion source for monitoring and detecting NOx emissions; provides reliable methods for detecting and monitoring of anthropogenic sources of NOx; also detection of NO in exhaled breath for patient health diagnosis.

15 Claims, 11 Drawing Sheets-

U.S. PATENT DOCUMENTS

| | | | |
|---|---|---|---|
| 4,025,818 | A | 5/1977 | Giguere et al. |
| 4,163,151 | A | 7/1979 | Bayless et al. |
| 4,201,921 | A | 5/1980 | McCorkle |
| 5,144,127 | A | 9/1992 | Williams et al. |
| 5,218,203 | A | 6/1993 | Eisele et al. |
| 5,420,424 | A | 5/1995 | Carnahan et al. |
| 5,455,417 | A | 10/1995 | Sacristan |
| 5,536,939 | A | 7/1996 | Freidhoff et al. |
| 5,654,544 | A | 8/1997 | Dresch |
| 5,723,861 | A | 3/1998 | Carnahan et al. |
| 5,763,876 | A | 6/1998 | Perinarides et al. |
| 5,789,745 | A | 8/1998 | Martin et al. |
| 5,801,379 | A | 9/1998 | Kouznetsov |
| 5,834,771 | A | 11/1998 | Yoon et al. |
| 5,838,003 | A | 11/1998 | Bertsch et al. |
| 5,965,882 | A | 10/1999 | Megerle et al. |
| 6,066,848 | A | 5/2000 | Kassel et al. |
| 6,124,592 | A | 9/2000 | Spangler |
| 6,323,482 | B1 | 11/2001 | Clemmer et al. |
| 6,417,511 | B1 | 7/2002 | Russ, IV et al. |
| 6,495,823 | B1 | 12/2002 | Miller et al. |
| 6,504,149 | B1 | 1/2003 | Guevremont et al. |
| 6,512,224 | B1 | 1/2003 | Miller et al. |
| 6,599,253 | B1 * | 7/2003 | Baum et al. ............... 600/532 |
| 6,621,077 | B1 | 9/2003 | Guevremont et al. |
| 6,744,043 | B1 | 6/2004 | Loboda |
| 6,822,224 | B1 | 11/2004 | Guevremont |
| 6,825,461 | B1 | 11/2004 | Guevremont |
| 2001/0030285 | A1 | 10/2001 | Miller et al. |
| 2002/0070338 | A1 | 6/2002 | Loboda |
| 2002/0134932 | A1 | 9/2002 | Guevremont et al. |
| 2003/0020012 | A1 | 1/2003 | Guevremont et al. |
| 2003/0038235 | A1 | 2/2003 | Guevremont et al. |
| 2003/0070913 | A1 | 4/2003 | Miller et al. |
| 2003/0089847 | A1 | 5/2003 | Guevremont et al. |
| 2004/0232326 | A1 | 11/2004 | Guervremont |

FOREIGN PATENT DOCUMENTS

| | | |
|---|---|---|
| WO | WO 96/19822 | 6/1996 |
| WO | WO 00/08454 | 2/2000 |
| WO | WO 00/08455 | 2/2000 |
| WO | WO 00/08456 | 2/2000 |
| WO | WO 00/08457 | 2/2000 |
| WO | WO 01/08197 A1 | 2/2001 |
| WO | WO 01/22049 A2 | 3/2001 |
| WO | WO 01/35441 A1 | 5/2001 |
| WO | WO 01/69220 A2 | 9/2001 |
| WO | WO 01/69647 A2 | 9/2001 |
| WO | WO 02/071053 A2 | 9/2002 |
| WO | WO 02/083276 A1 | 10/2002 |
| WO | WO 03/005016 A1 | 1/2003 |
| WO | WO 03/015120 A1 | 2/2003 |

OTHER PUBLICATIONS

Buryakov, I.A. et al., "A New Method of Separation of Multi–Atomic Ions by Mobility at Atmospheric Pressure Using a High–Frequency Amplitude–Asymmetric Strong Electric Field," International Journal of Mass Spectometry and Ion Processes (1993), pp 143–148, 128.

Carnahan, B. et al., "Field Ion Spectrometry—A New Analytical Technology for Trace Gas Analysis," ISA, (1996), pp 87–96, 51(1).

Carnahan, B. et al., "Field Ion Spectrometry—A New Technology for Cocaine and Heroin Detection," SPIE, (1997), pp 106–119, 2937.

Eiceman, G.A., et al., "Miniature radio–frequency mobility analyzer as a gas chromatographic detector for oxygen–containing volatile organic compounds, pheromones, and other insect attractants," J. Chromatography, (2001), pp 205–217, 917.

Guevremont, R. and Purves, R., "High Field Asymmetric Waveform Ion Mobility Spectometry–Mass Spectrometry: An Investigation of Leucine Enkephalin Ions Produced by Electrospray Ionization," J. Am. Soc. Mass. Spectrom, (1999), pp 492–501, 10.

Guevremont, R. et al., "Calculation of Ion Mobilities From Electrospray Ionization High Field Asymmetric Waveform Ion Mobility Spectrometry Mass Spectrometry," Journal of Chemical Physics, (2001), pp 10270–10277, 114(23).

Guevremont, R. et al., "Atmospheric Pressure In Focusing in a High–Field Asymmetric Waveform Ion Mobility Spectrometer," Review of Scientific Instruments, (1999), pp 1370–1383, 70(2).

Handy, Russell et al., "Determination of nanomlar levels of perchlorate in water by ESI–FAIMS–MS," JAAS (2000), pp 907–911, 15.

Hathout, Y., et al., "Identification of Bacillus Spores by Matrix–Assisted Laser Desorption Ionization Mass Spectrometry," Appl. Environ. Microbiol. 65(10):4313–4319 (1999).

Krylov, E.V., "A Method of Reducing Diffusion Losses in a Drift Spectrometer," Technical Physics, (1999), pp 113–16, 4d(1).

Krylov, E.V., "Pulses of Special Shapes Formed on a Capacitive Load," Instruments and Experimental Techniques, (1997), pp 628, 40(5).

Miller, R.A. et al., "A MEMS Radio–Frequency Ion Mobility Spectrometer for Chemical Agent Detection," (Jun. 2000) Proceedings of the 2000 Solid State Sensors and Actuators Workshop, Hilton Head, SC.

Miller, R.A. et al., "A MEMS radio–frequncy ion mobility spectrometer for chemical vapor detection," Sensors and Actuators, (2001), pp 301–12, A91.

Miller, R.A. et al., "A Novel Micromachined High–Field Asymmetric Waveform–Ion Mobility Spectrometer," Sensors and Actuators B, (2000) pp 300–306, B67 (3).

Pilzecker, P. et al., "On–Site Investigations of Gas Insulated Substations Using Ion Mobility Spectrometry for Remote Sensing of SF6 Decomposition," IEEE, (2000), pp 400–403.

Riegner, D.E. et al., "Qualitative Evaluation of Field Ion Spectrometry for Chemical Warfare Agent Detection," Proceedings of the ASMS Conference on Mass Spectrometry and Allied Topics (Jun., 1997), pp 473A–473B.

Schneider, A. et al., "High Sensitivity GC–FIS for Simultaneous Detection of Chemical Warfare Agents," Mine Safety Appliances Co., Pittsburgh, PA, USA, (2000), AT–Process, pp 124–136, 5(3,4), CODEN: APJCFR ISSN: 1077–419X.

* cited by examiner

| | TOTAL AMOUNT | EI eV | EA eV | PA KJ/mol | POSITIVE IONS | NEGATIVE IONS |
|---|---|---|---|---|---|---|
| NITRIC OXIDES:<br>NO<br>NO2 | 200ppm | 9.3<br>9.5 | 0.026<br>2.3 | 531<br>591 | YES<br>YES | NO<br>YES |
| H2O | 10% | 12.6 | - | 691 | NO | NO |
| OXYGEN | 9% | 12.06 | 0.45 | 421 | NO | YES |
| CO2 | 5% | 13.77 | -0.6 | 540 | NO | NO |
| HYDROCARBONS:<br>METHANE<br>PROPANE AND<br>PROPENE | 490ppm<br>625ppm | 12.61<br>10.94<br>9.73 | -<br>-<br>- | 543<br>625<br>751 | NO<br>NO<br>YES | NO<br>NO<br>NO |
| CO | 300ppm | 14.01 | 1.37 | 594 | NO | YES |
| HYDROGEN | 150ppm | 15.4 | - | 422 | NO | NO |
| ETHANE | 10ppm | 11.52 | - | 596 | NO | NO |
| NITROGEN | BALANCE | 15.58 | - | 493 | NO | NO |

FIG. 13

NOX MONITOR USING DIFFERENTIAL MOBILITY SPECTROMETRY

RELATED APPLICATIONS

This application claims priority to U.S. Provisional Application Ser. No. 60/418,235, filed Oct. 12, 2002, entitled FAIMS METHOD AND APPARATUS FOR NOX DETECTION AND ANALYSIS, by Raanan A. Miller, Erkinjon G. Nazarov, and Muning Zhong. The entire teachings of the above application are incorporated herein by reference.

BACKGROUND OF THE INVENTION

The present invention relates to spectrometry, and more particularly, to spectrometer devices providing chemical analysis by aspects of ion mobility in an electric field.

Chemical detection systems are used in a wide array of applications. These devices may take samples directly from the environment, or may incorporate a front end device to separate compounds in a sample before detection. There is particular interest in providing a chemical detection system capable of accurate compound detection and identification, and which may be deployed in various venues, whether in the lab, in the workplace or in the field.

Mass spectrometers are well known as the gold standard of laboratory-based chemical identification. But they are relatively difficult to deploy in the field. Such systems operate at low pressures, resulting in complex systems, and the spectra output can be difficult to interpret, often requiring a highly trained operator.

At times a gas chromatograph (GC) is used as a front-end to an MS, with good results. But the GC-MS is not well-suited for small, low cost, fieldable instruments for real-time chemical detection. Nevertheless there is a continuing need for fieldable instruments generation of real-time detection data.

Detection of species of NOx is a good example of this need. It is well known that reactive nitrogen oxide species NOx such as NO, $NO_2$, and $NO_3$ play a major role in atmospheric chemistry. These species are important in the ozone and nitrogen cycles, which produce detrimental photochemical smog and acid rain. Tougher environmental regulations to reduce these levels in the atmosphere require higher performance detectors and monitors applied to anthropogenic sources of NOx (e.g. exhaust from internal-combustion engines, steel mill processing, power plant emissions, etc.) with higher sensitivity and faster response times. Enhancement of fuel economy of internal-combustion engines is another driver for the development of sensors which are able to precisely, and rapidly, monitor NOx levels in exhaust emissions.

The medical value of detection of NO in exhaled breath has also been recognized for clinical diagnosis. For example, it has been reported that such clinical analysis can provide a noninvasive window into the activities of disease, such as asthma, chronic obstructive pulmonary disorder, and cystic fibrosis, in the lower airways. There is therefore a desire for improved, portable and simple apparatus and method for evaluation of NO in exhaled breath for medical purposes.

There are a number of reliable measurement techniques which have been developed for monitoring nitrogen oxide species: These include ion-based detection, chemiluminesence, electrochemical, acoustic gas sensors, and $ZrO_2$ solid electrolyte sensors, laser systems, and the like. These techniques, however, generally require sophisticated optical equipment, or suffer from significant drawbacks such as slow response times, or the detection of only certain NOx species, making them problematic for routine measurements.

Ion Mobility Spectrometry (IMS) has been explored recently as an approach to realizing a more sensitive, selective and robust device for NOx monitoring. In dry (humidity~10 ppm) operating conditions, the IMS shows high sensitivity (10's of ppms) and fast response times (10's of ms). However, a serious disadvantage is that its response is highly affected by the presence of moisture. For example, in one demonstration, a level of 3% humidity completely suppressed IMS response to a sample at 483 ppm $NO_2$.

Time-of-flight Ion Mobility Spectrometers (TOF-IMS) are considered to be functional chemical detectors. High-speed response and low memory effects have been attained, and the gas phase ion chemistry inside the TOF-IMS can be highly reproducible. Widespread use, however, still remains a problem for TOF-IMS. Among other things, TOF-IMS flow channels (also referred to as drift tubes) are still comparatively large and expensive and suffer from losses in detection limits when made small.

The differential ion mobility spectrometer ((DMS), also known as a high field asymmetric waveform ion mobility spectrometer (FAIMS)), is an alternative to the IMS. In a DMS device, a gas sample that contains a chemical compound is subjected to an ionization source. Ions from the ionized gas sample are drawn into an ion filter region, where the ions flow in a compensated high asymmetric RF field generated between filter electrodes, the field being transverse to the ion flow. The field is compensated to allow selected ion species to pass through the filter, based on aspects of their mobility in the field. These ion species are passed downstream to an ion detector. Detections are correlated with field conditions and compensation and species identification is made by reference to known species behavior in the extant compensated DMS field.

The asymmetric field alternates between a high and low field strength condition that causes the ions to move in response to the field according to their mobility characteristics. Typically the mobility in the high field differs from that of the low field. That mobility difference produces a net transverse displacement of the ions as they travel in the gas flow through the filter. This transverse travel of the ions continues until they drive into one of the filter electrodes and are neutralized. However, the field is also compensated such that a particular ion species will remain toward the middle of the flow in the flow path and will pass through the filter without neutralization. The amount of change in mobility in response to changes in the asymmetric field is compound-dependent. This permits separation of ions from each other according to their species based on the applied compensation (usually a dc bias applied to the filter electrodes).

In the past, Mine Safety Appliances Co. (MSA) made an attempt at a functional cylindrical FAIMS device with coaxial electrodes, such as disclosed in U.S. Pat. No. 5,420,424. (This FAIMS technology is referred to by MSA as Field Ion Spectrometry (FIS).) The device has been found to be complex, with many parts, and somewhat limited in utility.

It is a therefore an object of the present invention to provide a functional, small, spectrometer that overcomes the limitations of the prior art.

It is another object of the present invention to provide a chemical sensor with fast response times for real-time process control, especially for detection and identification of NOx related species in real-time.

It is another object of the present invention to provide a chemical sensor for detection and identification of NOx related species in real-time with minimized effect of moisture upon detection results.

It is yet another object of the present invention to provide low cost and compact, reliable instrumentation that is useful for laboratory and field conditions and is capable of making in situ measurements of chemicals present in complex mixtures at various venues.

SUMMARY OF THE INVENTION

The present invention achieves non-radioactive detection and identification of trace amounts of NOx species in a gas sample. In various embodiment of the invention, method and apparatus (i.e., systems) are provided for non-radioactive detection and quantification of NOx in a gas sample. Systems of the invention are compact, with fast response times (msec scale), high sensitivity and specificity, and low manufacturing cost. Devices of the invention are capable of being mass-produced with broad applicability.

Systems of the invention can detect positive NO spectra and negative $NO_2$ (and even $NO_3$) spectra. This detection can be performed simultaneously in a single scheme. Also, total NOx can be detected upon addition of $O_2$ gas to the sample to be scanned.

In practice of the invention of preferred embodiments of the invention, it is possible to detect NOx constituents in a single analytical scheme. A simple, practice of the invention includes Differential Mobility Spectrometry (DMS) systems which operate rapidly and can provide analytical information in real-time. These systems preferably feature non-radioactive ionization, which may be by means of a UV lamp, by corona discharge, by plasma, or by other photon sources. Use of a non-radioactive ionization source reduces risk to users and avoids regulatory issues as well as reducing the ionization energy to a level that avoids fragmenting or otherwise damaging the sample analytes to be detected.

Illustrative applications of the invention include detection of NOx in combustion exhaust gas for environmental monitoring purposes or as part of a controller for improving the combustion process. Such innovation addresses the analytical challenge posed by increasingly strict environmental regulations applied to anthropogenic sources of NOx (e.g., exhaust from internal-combustion engines, steel mill processing, power plant emissions, etc.).

Still another illustrative application of the invention includes a system for non-radioactive detection of NO in exhaled breath. Such detection system enables non-invasive and real-time patient health evaluations, and can be provided in a compact and low-cost package.

It has also been found that DMS practices of the invention minimize the affect of moisture on analyte detection. In one practice of the invention, moisture in a NOx sample does not affect DMS response up to about 1000 ppm and above 1000 ppm the compensation voltage increases with increasing humidity. Quite advantageously, this results in an enhanced resolving ability of the DMS in with varying levels of moisture.

In an illustrative DMS practice of the present invention, a gas sample is ionized. Ions from the ionized gas sample are drawn into a DMS ion filter and are subjected to differential ion mobility filtering to determine presence and amount of NOx.

This DMS filtering accentuates differences in ion mobility of the ionized sample in a high-low alternating asymmetric RF field. The filter field is compensated such that selected ion species are allowed through the field and are passed to an ion detector. Passing of an ion species is based on high field ion mobility characteristics of the species in the changing filter field conditions. All other species are neutralized within the filter.

Ion species identification itself follows upon downstream detection of the passed ion species and comparison of detection results against known detection behavior for the particular field conditions. In a preferred embodiment of the invention, positive and negative ion species are detected simultaneously.

Embodiments of the invention employ compact DMS systems made according to the principles of 1) U.S. Pat. No. 6,495,823, entitled MICROMACHINED FIELD ASYMMETRIC ION MOBILITY FILTER AND DETECTION SYSTEM, by Raanan A. Miller and Erkinjon G. Nazarov, incorporated herein by reference, 2) U.S. patent application Ser. No. 10/187,464, filed Jun. 28, 2002, internal Attorney Docket M070, entitled SYSTEM FOR COLLECTION OF DATA AND IDENTIFICATION OF UNKNOWN ION SPECIES IN AN ELECTRIC FIELD, by Lawrence A. Kaufman, Raanan A. Miller, Erkinjon G. Nazarov, Evgeny Krylov, Gary Eiceman, incorporated herein by reference, and/or 3) U.S. patent application Ser. No. 10/462,206, entitled SYSTEM FOR COLLECTION OF DATA AND IDENTIFICATION OF UNKNOWN ION SPECIES IN AN ELECTRIC FIELD, by Lawrence A. Kaufman, Raanan A. Miller, Erkinjon G. Nazarov, Evgeny Krylov, Gary Eiceman, incorporated herein by reference.

These and other aspects of the present invention are set forth below.

BRIEF DESCRIPTION OF THE DRAWINGS

The disclosed and other objects, features and advantages of the invention will be apparent from the following description of illustrative and preferred embodiments of the invention, and as illustrated in the accompanying drawings in which like reference characters refer to the same parts throughout the different views. The drawings are not necessarily to scale, emphasis instead being placed upon illustrating the principles of the invention, wherein:

FIG. 2(a–d) shows four related DMS scans of an NOx sample: (a) showing presence of NO and NO2, in N2 carrier gas; (b) same, with 1% O2 added to carrier; (c) same, taken 4 seconds after O2 removed from gas flow of (b); and (d) same, 18 seconds after shut off of O2 of (b).

DETAILED DESCRIPTION OF A PREFERRED EMBODIMENT

We are able to detect NOx, NO2, N2O4, HNO3, among other constituents, in a gas sample of NOx, and we are able to distinguished between such constituents in a single analytical framework. Systems of the invention obtain actual measurement of NOx activity in a changing environment in real-time. Applications include combustion control, whether for automotive engines or commercial furnaces or locomotives, or marine engines or the like, or medical tools, for example.

Figure 1A:
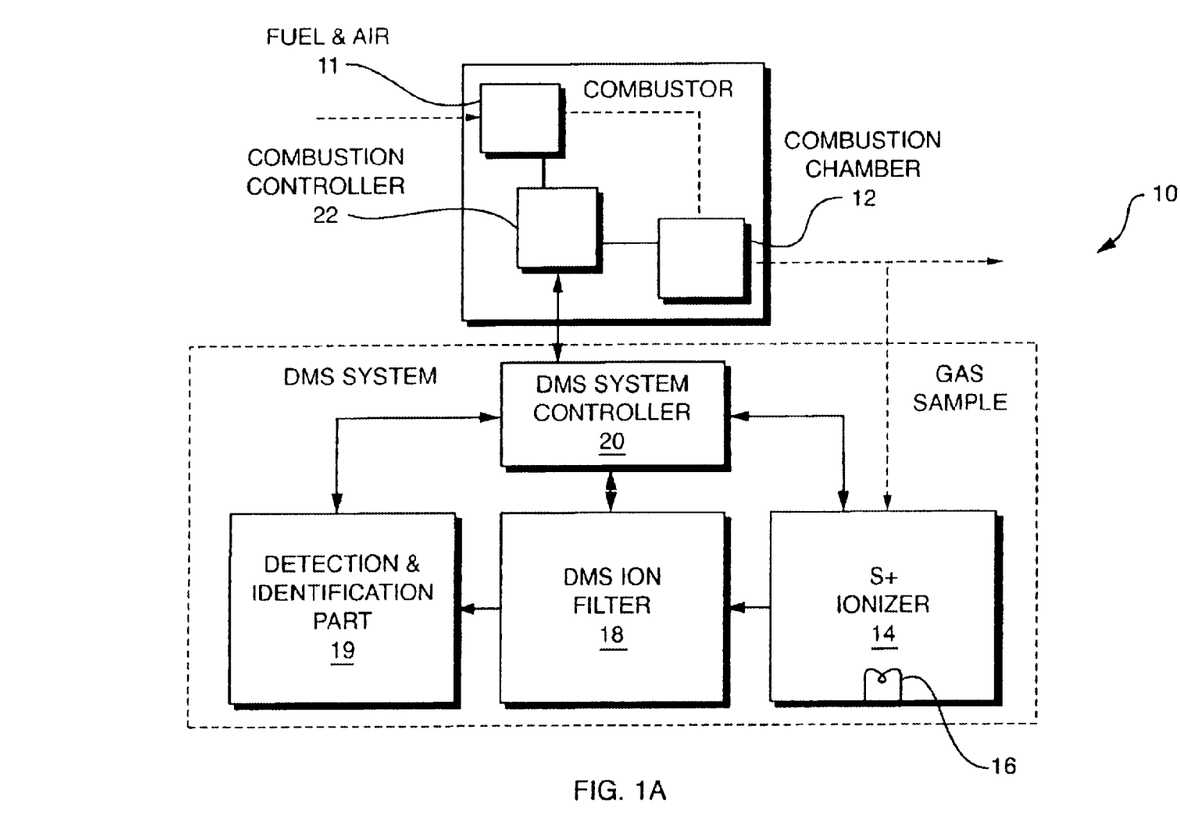
FIG. 1A is a diagram of a fast DMS combustion control system in practice of the invention.

Turning to FIG. 1A, in a preferred illustrative embodiment of the invention, a DMS system 10 is coupled to a combustor 11 (such as in a factory or generator or an automotive engine or the like) for real-time control of combustion conditions resulting in cleaner combustion and improved fuel economy. Fuel and air are drawn into the combustor and are mixed under control of a combustion controller and are combusted in a combustion chamber 12. Exhaust from the chamber includes many compounds. Of high interest is NOx and its constituents. For example, inefficient burning can result in emission of high levels of HNO3, which can result in acid rain. Detection of NO and NO2 is also important in controlling combustion.

In FIG. 1A, a sample of exhaust S from the combustion chamber 12 is drawn into an ionization chamber 14. Selection of an ionization source is important. We have found that a source that provides soft ionization conditions is best for NOx detection of combustion components. A higher energy source can result in ionization of the nitrogen in the background air and therefore can corrupt detection and analysis of NOx constituents of the combustion effluent. A non-radioactive source is therefore preferred. A UV source 16 provides adequate energy to ionize the target NOx without ionization of the nitrous background. A UV lamp is a conventional soft ionization source and would be adequate and even preferred in practices of the present invention.

In FIG. 1A, the sample is ionized in chamber 14 and the ionized sample $S^+$ is flowed into the DMS filter 18 wherein it is filtered according to known DMS principles, as earlier described. Species detection data from detector 19 is processed to enable identification of the NOx constituents. This process is managed under control of a DMS System controller 20. Based on such identification, a data signal is issued by the system controller 20 to the combustion controller 22 for improvement of fuel combustion. Such detection, identification and combustion adjustments are enabled by reference to a store of known system behavior, which may be incorporated within controller 20.

Because we can distinguish the effects of humidity on analytical results, we can provide real-world, real-time and accurate detection of NOx and its constituents, unlike IMS systems. Therefore, the combustion controller of the invention performs combustion control functions which can be used to improve combustion efficiency in real-time and in real-life environments, in situ, as will be fully appreciated by a person skilled in the art.

Figure 1B:
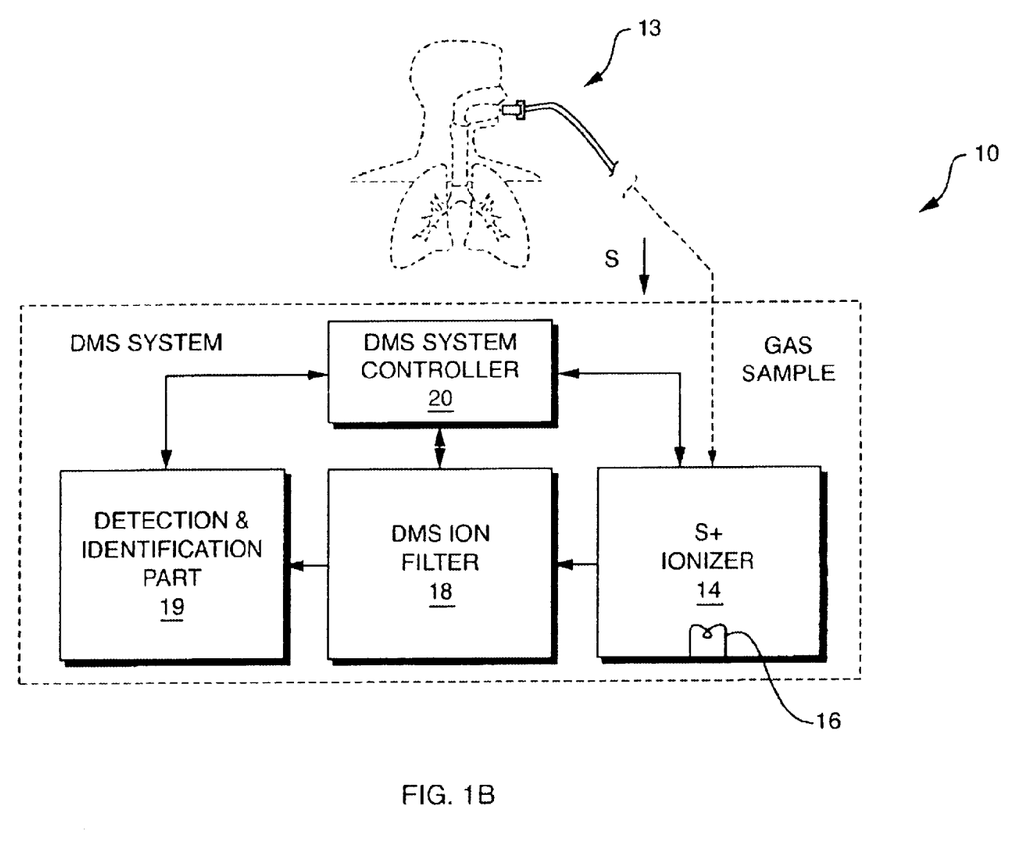
FIG. 1B is a diagram of a fast DMS system for breath analysis.

Other embodiments of the invention enable portable medical equipment for detection of NO in patient breath as a non-invasive diagnostic, such as for of lower airway diagnosis. Turning to FIG. 1B, a patent breath output is captured as sample S and is introduced into a DMS system 10 by a exhale capture device 13 for real-time detection of NO in the patent's breath. As in FIG. 1A, sample S is drawn into an ionization chamber 14 and ionization, filtering, detection and identification proceed accordingly. In an illustrative application, daily measurements of NO in the breath can be used to regulate medication, such as glucocorticoids, for such diseases as asthma.

Figure 2A:
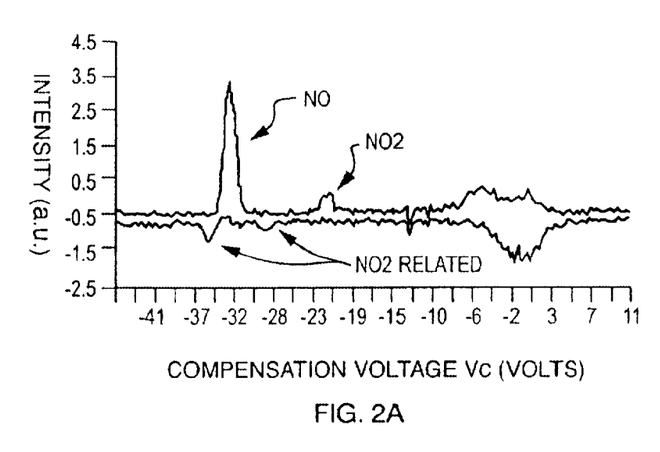
Figure 2B:
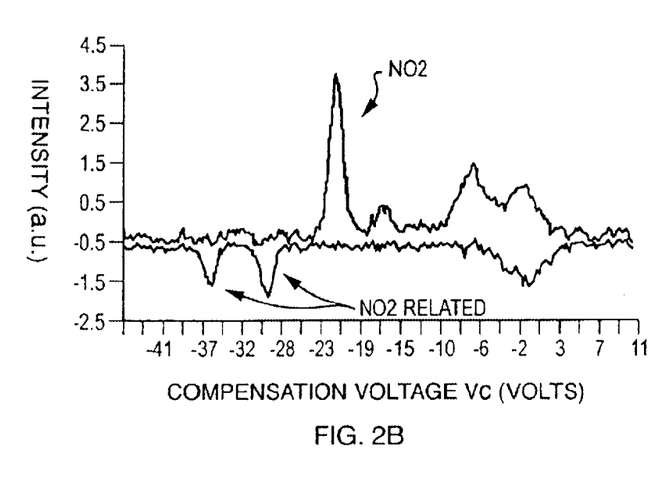
Figure 2C:
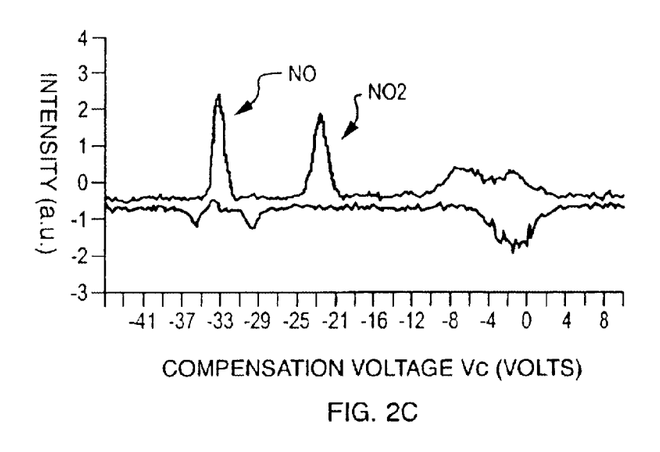
Figure 2D:
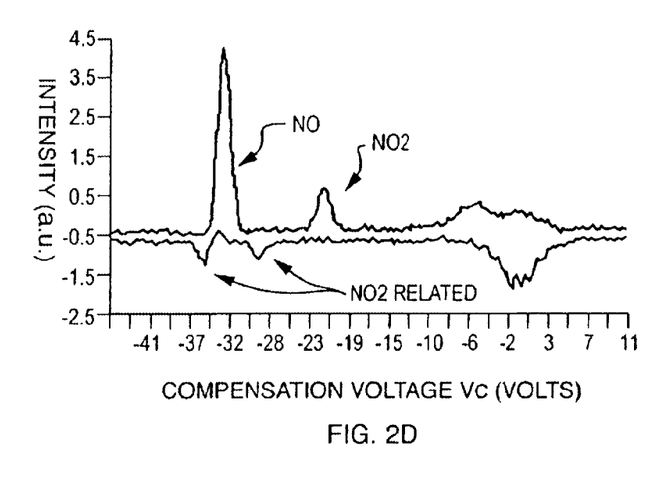

An Illustration of the Invention:

An illustrative operation of the invention is discussed with reference to FIG. 2, in which four related DMS scans of a NOx sample are shown (Frames a-d). FIG. 2(*a*) shows presence of NO and NO2 in N2 carrier gas (flow rate of 6 ppm) and is a plot of intensity versus compensation voltage in the DMS filter with detection of NO at intensity of about 3.5 at about −32v compensation and with trace NO2 at about −20v.

In FIG. 2(*b*) the conditions of FIG. 2(*a*) were repeated but with 1% O2 added to the gas flow. Reaction of the NOx and O2 results in formation of NO2, as indicated by several intensity peaks (as shown by the arrows) at several compensation levels. It will be observed that the 1% O2 resulted in essentially total conversion of NO to NO2 in this situation.

In FIG. 2(*c*) the conditions of FIG. 2(*a*) were repeated but and a reading was taken 4 seconds after the O2 was removed from the gas flow. Owing to some latency in the system, some amount of O2 remains in the flow path as indicated by the moderate presence of NO2 detected at about −21 compensation, and the return of NO as seen at −33 compensation.

In FIG. 2(*d*), the conditions of FIG. 2(*a*) were repeated but with 1% O2 added to the gas flow and the detection was made 18 seconds after shut off of the O2. FIG. 2(*d*) shows that the O2 has cleared the flow path 18 seconds after it was removed from the flow. No attempt was made to accelerate this clearing, as might be done by heating or other purging processes. Nonetheless, this shows that the system has purged and nearly returned to the condition of FIG. 2(*a*). Furthermore, under realistic operating conditions, at elevated temperatures, the sample would be purged all the more readily.

Each of these frames shows both positive and negative mode detections for the NOx constituents of the sample in practice of the invention. Positive and negative mode detections are made in practice of a preferred compact DMS embodiments of the invention as taught in Ser. No. 10/187,464, as incorporated herein.

It will thus be appreciated that in practice of the invention, a controlled gas flow can be used for detection of NOx and its constituents, and that such is achieved with high resolution and specificity. This process is both repeatable and predictable.

EXAMPLES

Ion energy considerations for photo-ionization and ion formation of NOx species in air at atmospheric pressure in practice of the invention are provided below. First, an understanding of the ion energetics and ion chemistry is provided, as this is part of the understanding of operation of the preferred DMS method and apparatus of the invention and is a foundation for interpreting the resulting spectra.

Figure 13:
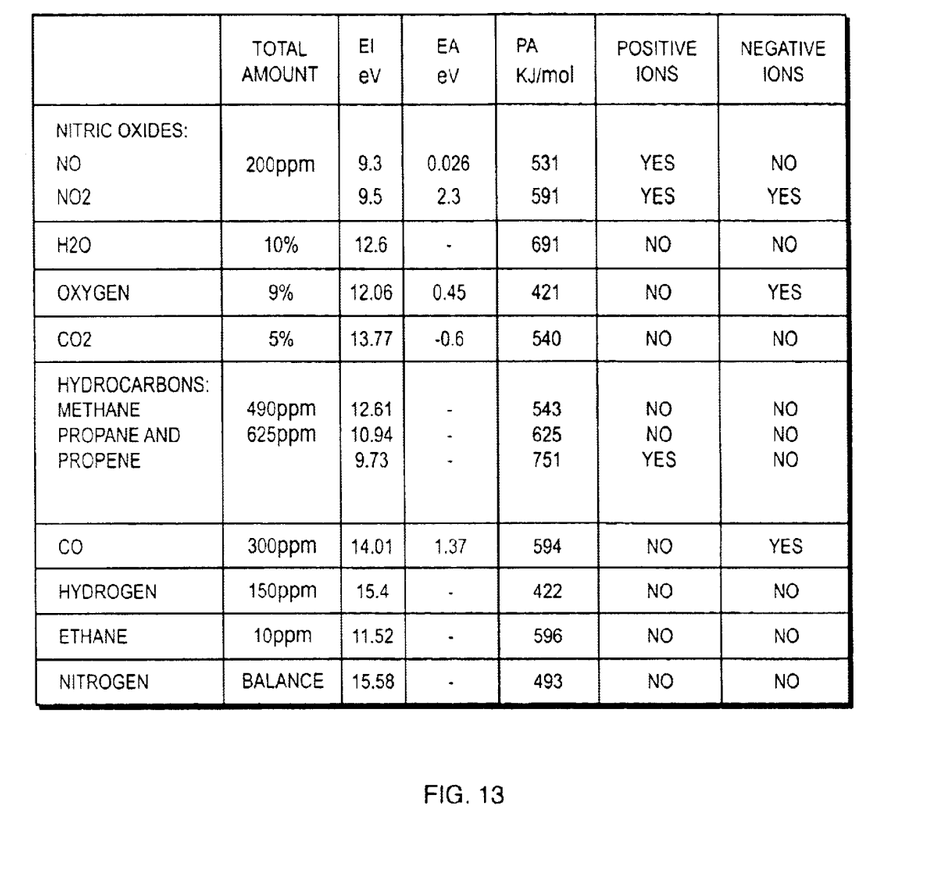
FIG. 13 is a table of ionization energies and proton and electron affinities.

As an illustration, FIG. 13 shows the typical chemical composition of an engine exhaust. Select ion energy properties of these components are: ionization energy (EI), electron (EA) and proton affinity (PA), and potential for ion formation via a UV ionization source with photon energy of 10.67 eV.

Analysis of the data from FIG. 13 shows that only NO, $NO_2$, and propene species have an ionization energy lower than the photon energy (10.6 eV) provided by the UV ionization lamp used in this work. Consequently only these three components of the exhaust gas will directly form ions, in this case positive ions. The other components cannot directly form ions. However, there are other pathways for ion formation at atmospheric pressure due to proton and electron charge exchange reactions. For example in the positive mode, due to proton transfer reactions, we expect formation of ion species with the highest proton affinity. These are propene and protonated water cluster ions. In the negative mode, ion formation will occur as follows: free electrons which are formed due to photo-ionization of NOx and propene molecules, at atmospheric pressure conditions, will be captured by components which have positive electron affinity. In our experimental conditions, it may be oxygen, CO, and nitrogen dioxide molecules. $NO_2$ molecules have significantly higher proton affinity compared with the other components. Given sufficient time all free electrons will be transferred to the nitrogen dioxide molecules. Therefore, based only on ion energetic arguments it is expected that with UV ionization, and monitoring of the DMS negative spectra, it should be possible to detect and monitor different levels of $NO_2$ in an exhaust stream.

In an illustrative practice of the invention with UV ionization, a Krypton filled UV lamp (PID Lamp λ=123.9 nm and 116.9 nm with energies 10.0 eV and 10.6 eV) was used. Standard gases includes NO 1500 ppm balanced with nitrogen, NO 1500 ppm, NO2 1500 ppm. Drift Gas was grade 5 nitrogen (99.9995%). The drift gas (nitrogen) was flowed at 1500 cc/min, with a range of DMS compensation voltage (CV) between −45V and +12V, with scan time at 1 sec. RF voltage was at 1200V. Scans to average=1, Steps to average=1, Number of steps/scan=250. Mass flow controllers (MFC) were used at 2000 cc/min, 100 cc/min, 50 cc/min and 10 cc/min for nitrogen and 50 cc/min for oxygen. Performance was at room temperature. Drift gas and NOx standard gases were introduced and mixed via MFCs at designated levels. Oxygen at 10% was introduced with a flow controller for NO/NO2 dynamic determination.

A preliminary set of control experiments was conducted prior to introduction of real samples. First, the DMS system was run with a transport gas of pure nitrogen to verify that the background spectrum was clean. As expected, no peaks were observed in both positive and negative modes. When small amounts of NOx samples were mixed with the transport gas, peaks appeared in the DMS spectra which behaved consistently with ion energetic considerations of the analytes. NO samples produced dominant positive ion peaks and $NO_2$ samples exhibited mostly negative ion peaks.

NO and $NO_2$ Spectra in Positive and Negative Modes

Figure 3A:
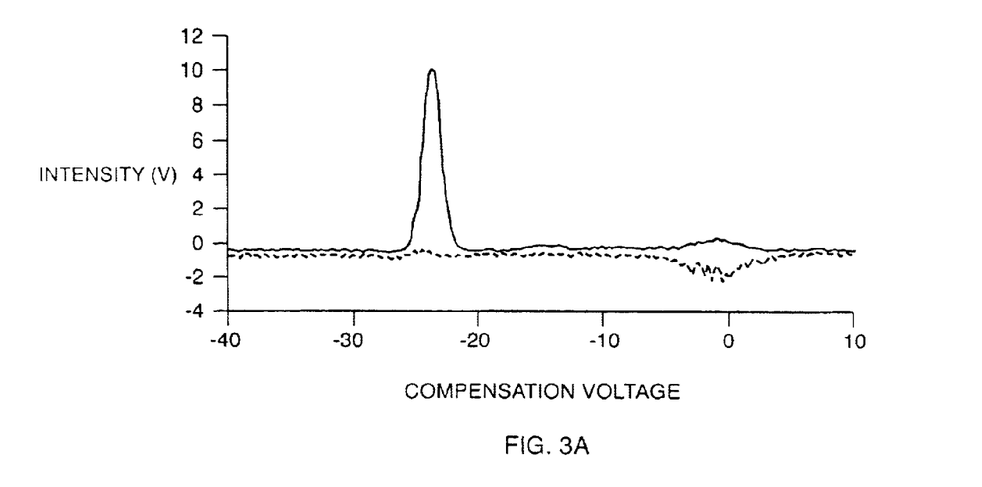
FIG. 3 shows spectra for (a) NO and (b) $NO_2$ in clean nitrogen transport gas, with RF voltage at 1200V; the upper scan shows the spectrum for positive ions and the lower scan shows the negative response in each.
Figure 3B:
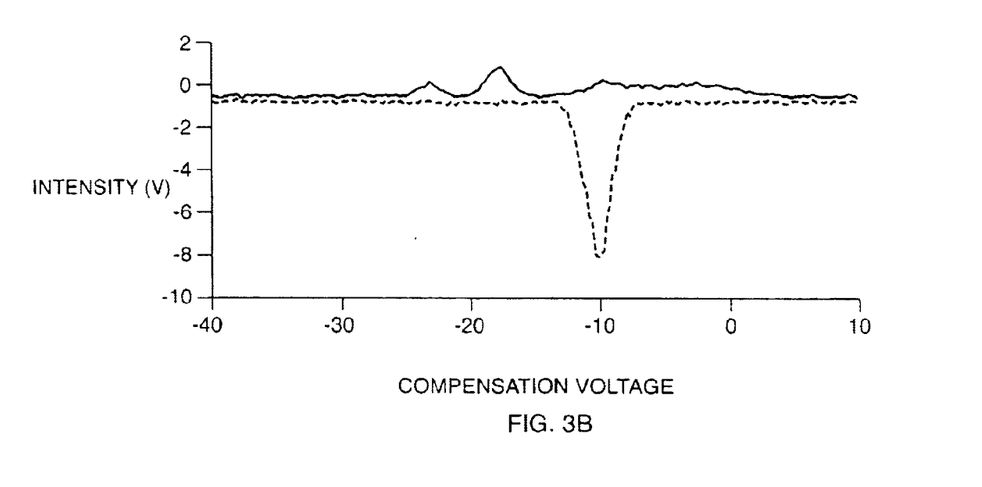

FIG. 3 shows individual spectra for NO (FIG. 3a) and $NO_2$ (FIG. 3b) samples. As expected, the NO sample spectra shows a single positive peak at Vc=−23V. The low intensity negative peak around Vc=0V is believed to be an impurity.

The $NO_2$ sample spectra showed a major single peak in the negative mode at Vc~−10V. Two peaks with relatively small intensities are also apparent in the positive polarity at Vc=−23V (same location as for the NO sample), and at Vc=−17V. These positive peaks are believed related to $NO^+$ and $NO_2^+$ and may be formed due to photolysis of the $NO_2$ molecules into NO, O, and a combination of these molecular species (e.g. $NO_3$), as shown in equation (1):

Because molecules of $NO_2$ and $NO_3$ have very high electron affinities (2.3 and 3.9 eV respectively), these species will capture electrons from the other compounds (including unidentified impurities) due to charge exchange processes, and form negative ion species. This may explain the presence of a stable single peak in the negative spectra. In this model the intensity of the negative peak should be proportional to the concentration of NOx in the gas mixture.

It is well known that mixtures of NO and $NO_2$ exist in dynamic equilibrium with their relative concentrations dependant on experimental conditions. FIG. 3 illustrates that the DMS has the ability to directly measure the amounts of both NO and $NO_2$ species actually existing in the mixture. The positive ion spectra, provides information on the NO species while the negative ion spectra provides information on the amount of $NO_2$ (or $NO_3$) species present. This was confirmed by a validating experiment performed by oxidizing NO. 10% of oxygen was added to the standard nitrogen transport gas and blended with the standard NO sample. This resulted in a decreased intensity of the positive NO ion peak at Vc=−23V and simultaneously an increase in the intensity of the positive ion peak at Vc=−17V. Meanwhile in the negative polarity, a new peak at Vc=−10V, related to $NO_2$ appeared. After the oxygen flow was turned off, the peaks transformed back to the characteristic NO spectra.

Concentration Dependences for NO and $NO_2$ Species

Figure 4A:
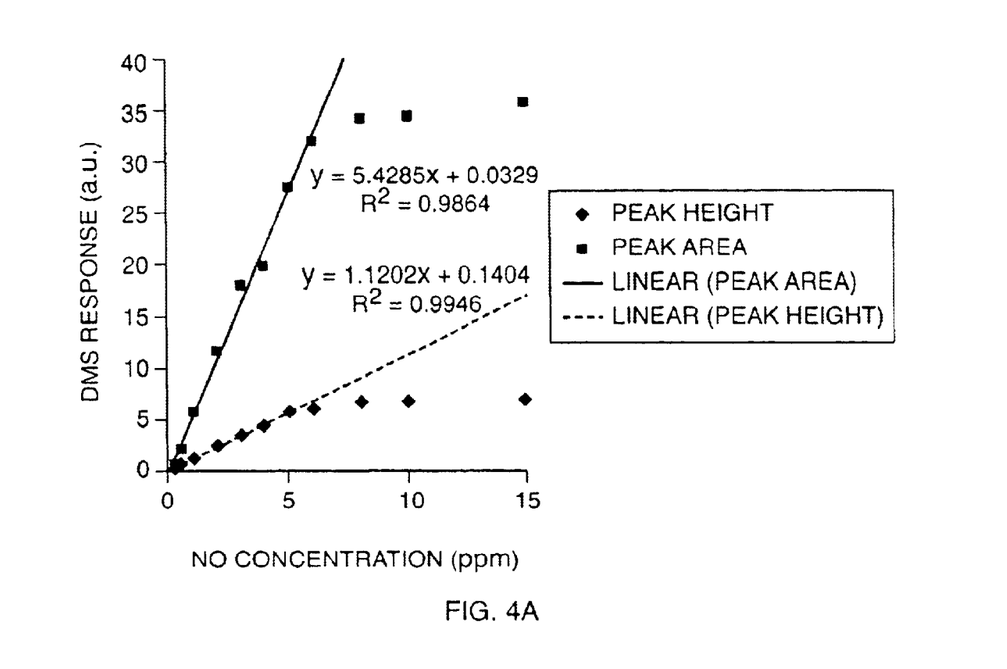
FIG. 4 shows concentration dependence of DMS for (a) nitric oxide and (b) nitrogen dioxide, comparing peak area (squares) to peak height (diamonds).
Figure 4B:
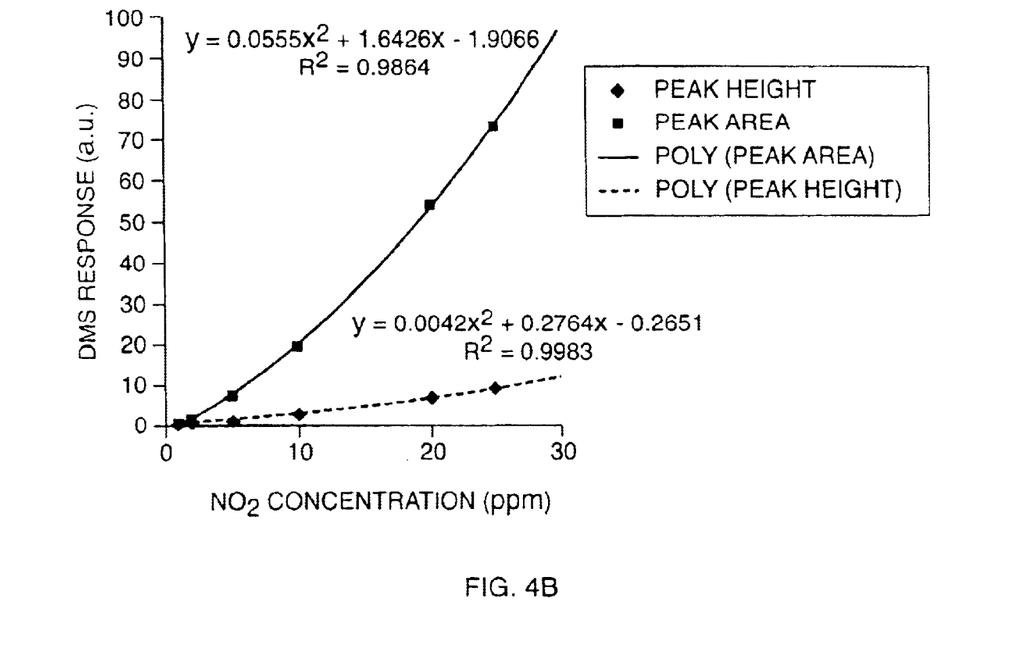

FIG. 4(a & b) shows the DMS intensity response to different concentrations of NO (positive polarity ions) and $NO_2$ (negative polarity ions) samples. Plots for peak height (blue) and for peak area (pink) are presented. One can see that for NO these plots have a linear range (Y=4.6x−6.1 e.g. for area) up to 6 ppm. The $NO_2$ plots are nonlinear but can be fitted very well by quadratic approximations ($Y=0.0055x^2+1.65x−1.9$ for area plot). The resulting reactions for positive and negative ion formation have different reaction orders. Positive ion formation has a first reaction order while the negative ion formation has a second reaction order. This means that the rate of negative ion formation is increased with increasing concentration of $NO_2$. One of the possible explanations is that in the negative mode NO and $NO_2$ are oxidized to $NO_3$ producing the negative spectral peak. The oxidation process may be enhanced due to the UV lamp radiation, according to reactions (1). Another mechanism which is specific for nitrogen dioxide is due to collision of neutral molecules of $NO_2$ with oxygen atoms resulting in their transformation from one molecule to other.

With increasing concentration of $NO_2$ the rate of this reaction increases due to increasing collision frequency. In this case, the amount of free electrons is increased due to ionization of NO resulting in positive ions (NO has the lowest ionization energy) and a second product $NO_3$ which has the highest electron affinity (3.9 eV). This results in a condition favoring increased efficiency of negative ion formation. The estimated limit of detection for both chemicals according to FIG. 4 are 0.3 ppm for NO and 1 ppm for $NO_2$.

NO and $NO_2$ Spectra in Positive and Negative Modes for Complex Transport Gases Laboratory tests were also conducted with more complex, and realistic, transport gases. The transport gas used had the following composition: 23.6 ppm of $SO_2$; 121.2 ppm of $H_2$; 398 ppm of CO, 8.1% of $O_2$; 10% of $CO_2$; with nitrogen as the balance gas. In this part of work the transport gas flow rate was 400 cc/min. As used, the $NO_2$ flow rate was constant at 5 cc/min and concentration of $NO_2$ in sample mixture was 1500 ppm. NO flow rate varied from 0.62 cc/min to 10 cc/min and concentration of NO in sample mixture was 1500 pp. FIG. 5(a,b,c,d) shows the results of these experiments.

Figure 5A:
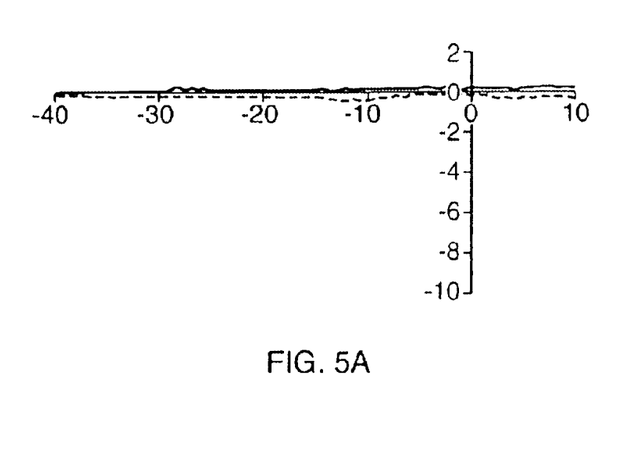
FIGS. 5a, 5b, 5c and 5d show DMS spectra for negative (lower traces) and positive (higher traces) ion species for NOx samples, with transport gas at a mixture of: 23.6 ppm of $SO_2$; 121.2 ppm of $H_2$; 398 ppm of CO, 8.1% of $O_2$; 10% of $CO_2$; and $N_2$ as the balance gas.
Figure 5B:
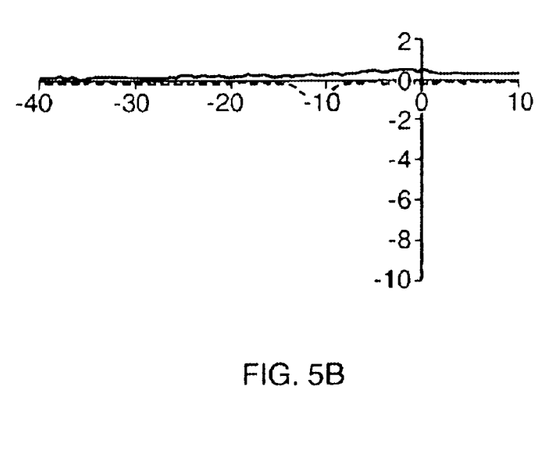
Figure 5C:
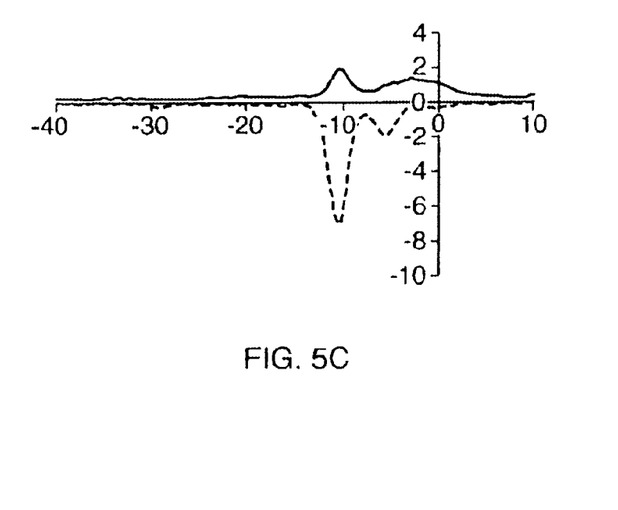
Figure 5D:
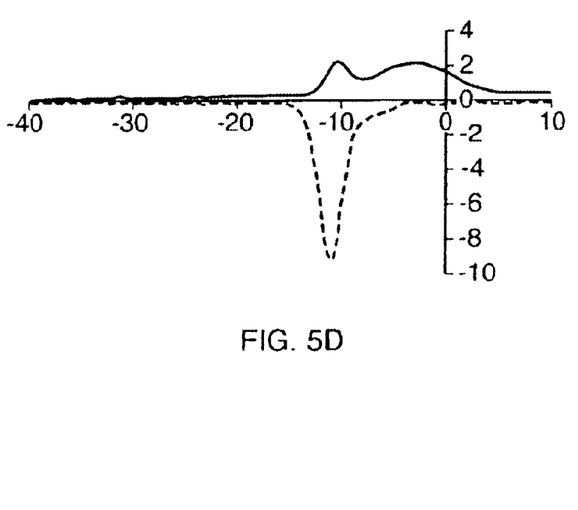

No peaks in both the positive and negative spectra are evident in the background gas mixture shown in FIG. 5a. This is because all the components of this gas mixture have significantly higher ionization energies than the photon energy provided by the UV lamp. Consequently, no positive or negative ions will form directly. After introduction of 18 ppm $NO_2$ the negative ion peak at Vc=−10.5V appeared, and only traces of the positive ions (see FIG. 5b) were seen. This condition is a similar to the case when only clean nitrogen transport gas was passed through the DMS (see FIG. 3b). When NO at 36 ppm was added, FIG. 5c, simultaneously both positive and negative ion peaks were observed. The positive ion peaks have different positions compared to when only the nitrogen transport gas is used, but the negative ion peak has the same compensation voltage seen for $NO_2$. One explanation of this result is due to the presence of oxygen (10%) which can oxidize the NO and produce neutral $NO_2$ (or $NO_3$). $NO_3$ has very high electron affinity and will form negative ions by direct capture of free electrons, or by electron exchange processes from negative ions of $O_2$ and CO which may have formed earlier but which have significantly lower electron affinities (EA). Simultaneous introduction of NO (36 ppm) and $NO_2$ (18 ppm) increases the intensity of the negative ion peak (see FIG. 5d).

Figure 6A:
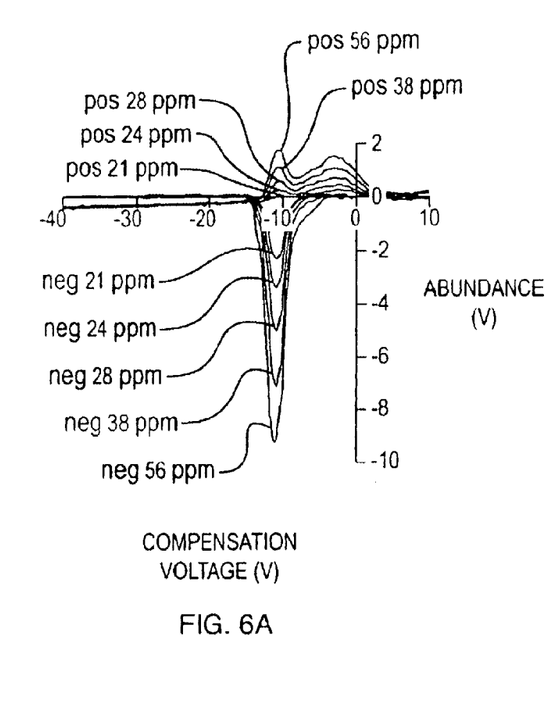
FIG. 6 shows the effect of changing NOx concentration on DMS Spectra.
Figure 6B:
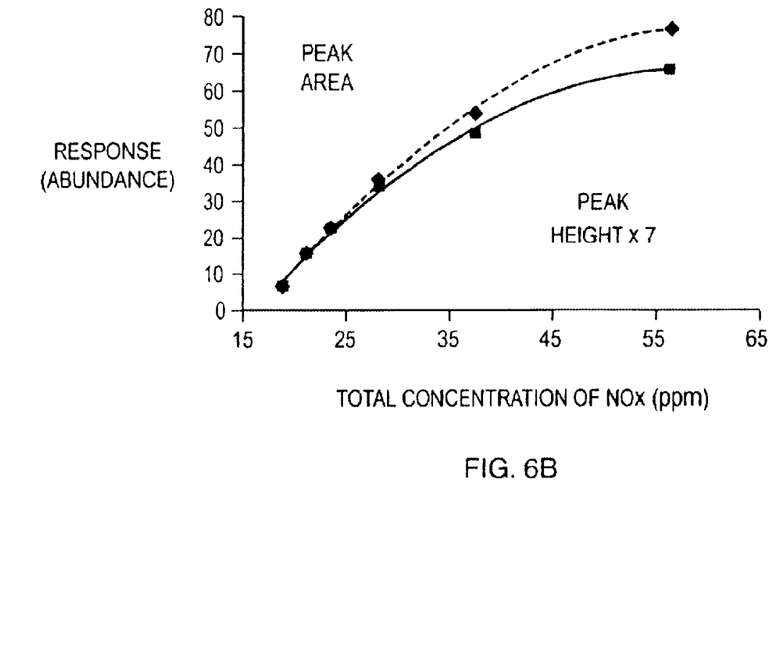

The response of the DMS to different total amounts of NOx is shown in FIG. 6a. One can see that the peak position for the negative ions remains the same, and only the peak intensity changes. Concentration dependence plots for peak area and peak height are shown in FIG. 6b. The two plots look similar, indicating that the peak form does not change. The estimated limit of detection for NOx under these conditions is around 2 ppm.

Effect of Moisture ($H_2O$) on DMS Negative Ion Spectra

Figure 7:
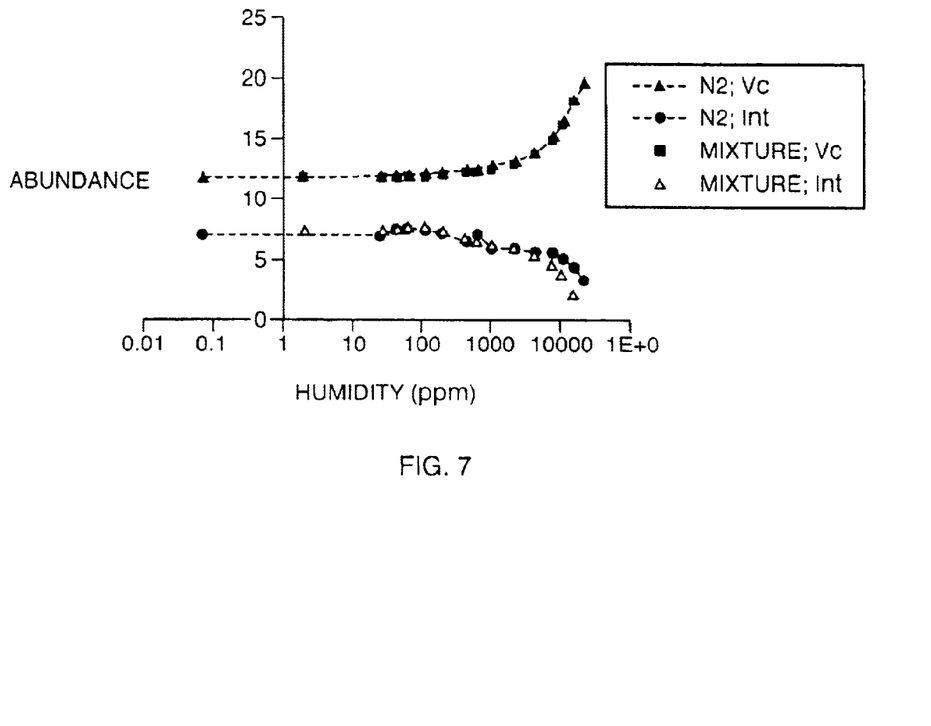
FIG. 7 shows the effect of humidity on negative mode NOx peak position and peak intensity for transport gases of clean nitrogen and the complex mixture discussed in section e.

One significant disadvantage of conventional IMS is the suppression of its response to NOx species as humidity levels increase. The DMS response to NOx species at different moisture levels was therefore closely studied. FIG. 7 shows results of peak position and peak intensity for the negative ions plotted at different moisture levels.

As is evident in FIG. 7, the moisture does not affect the DMS response up to about 1000 ppm. Above 1000 ppm the compensation voltage increases with increasing humidity, i.e., shifts the peak to a more negative value away from the zero axis. This results in an enhanced resolving ability of the DMS as the moisture level increases. The intensity of peak decreases, but rather gradually (increasing the moisture level from 1000 ppm (relative humidity 4%) to 21000 ppm (relative humidity 85%) changes the intensity from 6V down to 3.0V) as shown in FIG. 7. Results of varying the humidity produce similar peak positions shifts and peak intensities with both the mixture and nitrogen transport gases.

Effect of Propene on Detection of $NO/NO_2$

Figure 8:
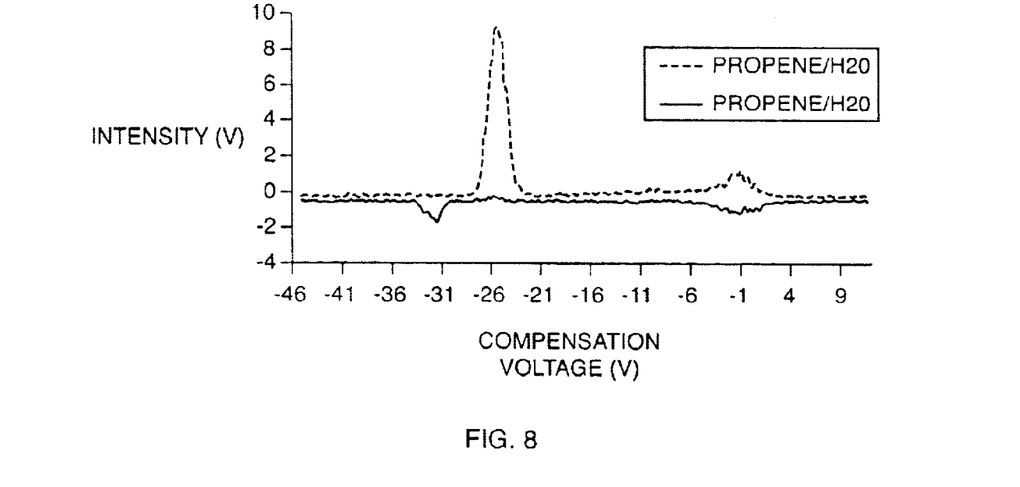
FIG. 8 shows the response of DMS to a transport gas composed of propene, O2, N2 and water.

Real exhaust typically contains many hydrocarbons. Propene is historically used as a representative compound for the hydrocarbon matrix in exhaust gas. FIG. 8 shows the DMS spectra for a transport gas containing 100 ppm propene, 10% oxygen in clean nitrogen with moisture at a 70C dew point.

Figure 9:
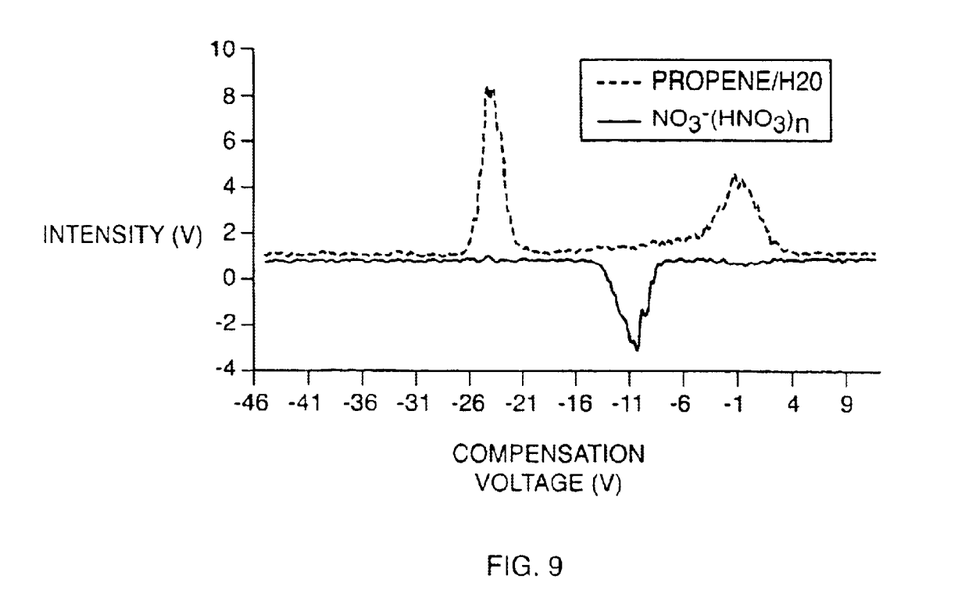
FIG. 9 shows the response of DMS when $NO_2$ and NO samples are added to the DMS transport gas.

The resultant spectra shows a propene peak in the positive mode at a compensation voltage of Vc=−26V. The main propene related peak in the negative mode is at a compensation voltage of Vc=−31V. When a sample of 100 ppm $NO_2$+20 ppm NO is introduced into the DMS, FIG. 9, the positive ion propene peak remains at Vc=−26V while the negative ion peak shifts to a compensation voltage of Vc=−11 volts. This peak is the same as the one observed for the $NO_2$ sample. From mass spectrometric analysis this peak has been determined to be an $NO_3$ related peak. Once again, the negative mode DMS spectra shows a characteristic response for the total NOx sample.

Mass Spectrometric Investigation of DMS Spectral Peaks

Figure 10:
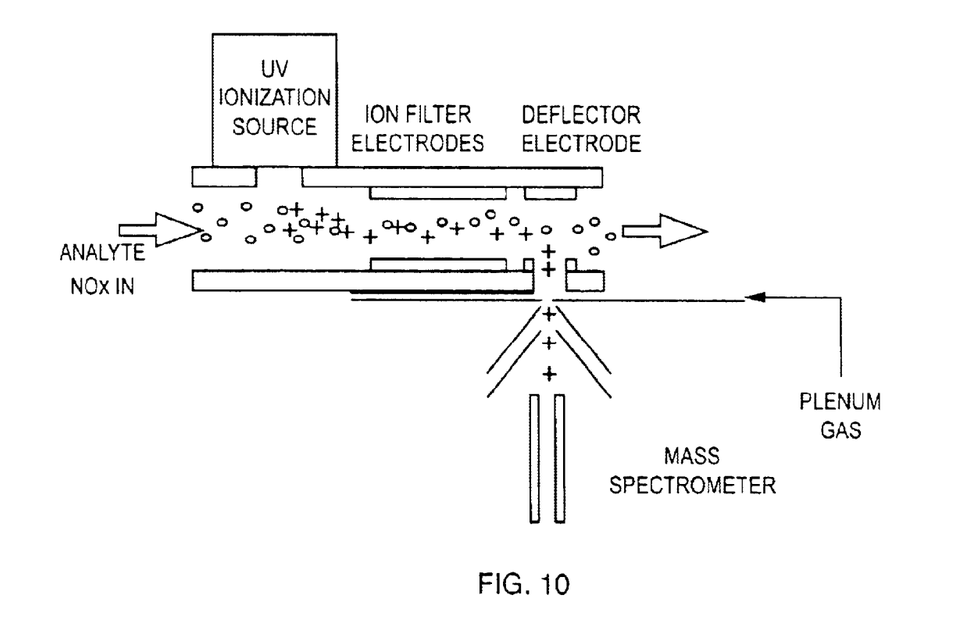
FIG. 10 is a schematic of an illustrative DMS/MS interface in application of the invention.

Analysis of the DMS spectra with NOx species shows that there are many possible pathways for formation of these ions in air, especially at ambient pressure. Spectra can contain derivative peaks of new species which are formed due to association, dissociation, fragmentation, oxidation and chemical reaction between molecules, fragments, and atmospheric gases. Therefore, validation experiments with direct chemical identification have been provided. For this purpose mass-spectrometric has been carried out. FIG. 1A0 shows a schematic of a preferred micromachined DMS coupled to a mass spectrometer.

A photo-ionization source was attached to the DMS sensor for ionization, and a Teflon base was interfaced to pneumatically attach the DMS to the flange of a TAGA 6000 APCI-tandem mass spectrometer (MS/MS) from Sciex, Inc. (Toronto, Ontario, Canada). The MS/MS was equipped with a computer and API Standard Software, Ver 2.5.1 (PE SCIEX). Analytes (NOx) were introduced with transport gas and ionized before introduction into ion filter region of the DMS. Once through the filter region, the ions were injected through a hole in the detector electrode, into the pinhole of the interface plate of the MS/MS. Polarity of injected MS ions could be changed by changing the polarity of the deflector electrode. The significant advantage of this interface is that, under the effect of the deflector voltage and mass-spectrometer plenum gas, the analyzed ions are completely isolated from analyte neutrals exhausted by the DMS transport gas. Another advantage of this interface is the possibility to simultaneously record DMS and MS spectra.

Figure 11A:
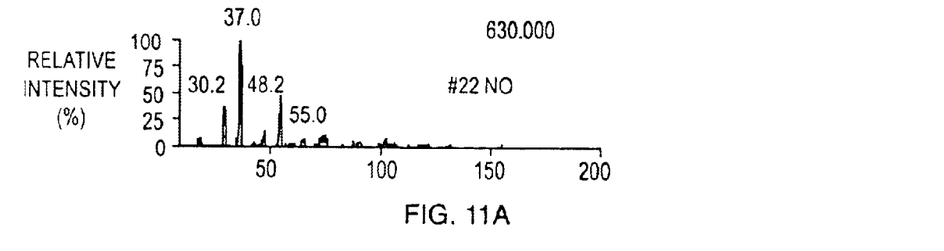
FIG. 11 shows mass-spectra for positive NOx ions: (a) 20 ppm of NO in dry $N_2$ transport gas, (b) 20 ppm of NO in dry $N_2+O_2$ (10%) transport gas, similar spectra obtained with $NO_2$ in dry $N_2$, and (c) 20 ppm of NO in humidified $N_2$ transport gas.
Figure 11B:
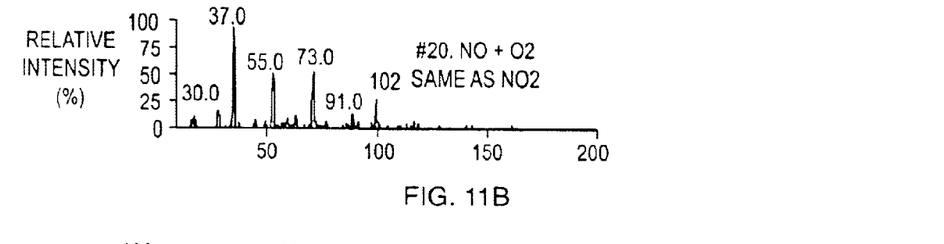

FIG. 11 shows positive ion mass spectra for 20 ppm NO in dry $N_2$, FIG. 11a, and FIG. 11b, when 10% of oxygen was added to the dry transport gas ($N_2$). When instead, NO the $NO_2$ samples were introduced mass-spectra similar to that of FIG. 11 was recorded. One can see that the NO mass-spectra contains two series of ions: related to monomer and cluster nitric oxide ions $W_nNO^+$ and proton bounded water ions $W_kH^+$. The level of water (W) clustering depends on the moisture level. For dry conditions, with humidity less than 10 ppm; the values of n and k may vary from 0 to 4. The nitric oxide peaks are M/z=30 $[NO^+]$, 48 $[(W)NO^+]$, 66$[(W)_2NO^+]$, 84$[(W)_3NO^+]$, 102$[(W)_4NO^+]$, and proton bound water peaks are M/z=19 $[W H^+]$, 37 $[(W)_2H^+]$; 55 $[(W)_3H^+]$; 73 $[(W)_4H^+]$.

Figure 11C:
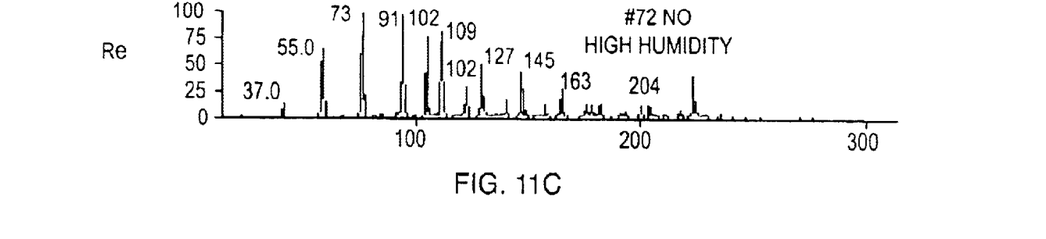

When humidity is higher, the level of clustering increases (see FIG. 11c). As a result the light nitric oxide monomer (m/z=30) and cluster (m/z=48) peaks disappear and heavier ions related to NO samples appear: $120[(W)_5NO^+]$; $138[(W)_6NO^+]$; $156[(W)_7NO^+]$; $174[(W)_8NO^+]$; $192[(W)_9NO^+]$; and $204[(W)_4NO^+]_2$. Likewise, heavier water clusters also appear: 91 $[W_5H^+]$; $109[W_6H^+]$; $127[W_7H^+]$; $145[W_8H^+]$; $163[W_9H^+]$; 181 $[W_{10}H^+]$; $199[W_{11}H^{30}]$.

Figure 12A:
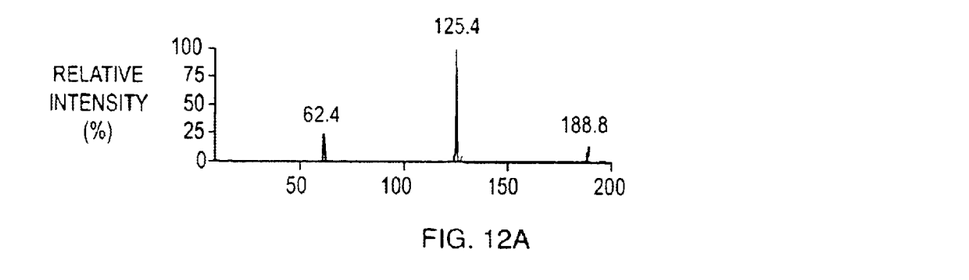
FIG. 12 shows mass-spectra for negative NOx ions: (a) 20 ppm of $NO_2$ in dry $N_2$; and (b) 20 ppm of NO in humidified $N_2$, and similar spectra when $NO_2$ sampling.
Figure 12B:
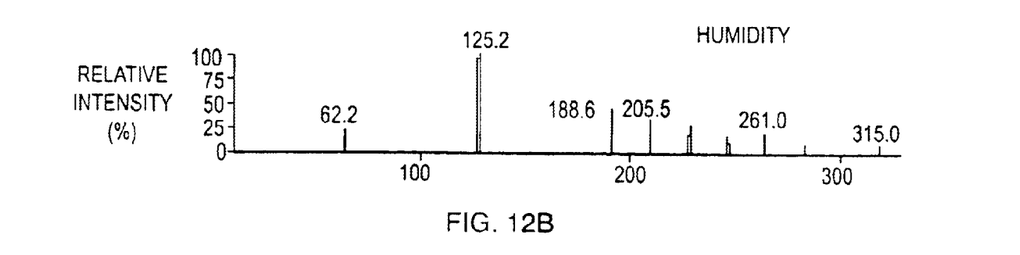

The nitrogen dioxide and nitric oxide positive ions mass spectra are significantly different. In contrast to NO, the nitrogen dioxide positive ion mass spectra (FIG. 11b) shows no specific peaks related to $NO_2$ [m/z=46]. The mass-spectrum contains mostly proton bound water cluster ions m/z=37,55,73,91, relatively low intensity peak m/z=30 $[NO^+]$, and m/z=102 $[W_4NO^+]$. The last two peaks show that a process of dissociation of $NO_2$ molecules to NO+O certainly exists. This is likely key to considering future oxidizing of $NO_2$ molecules to $NO_3$ by a series of chemical reaction steps (see, e.g. reactions (1)). The negative ion mass spectra for both samples, provides additional evidence for this mechanism. Mass spectra for both NO and $NO_2$ samples are similar and contain peaks m/z=62, 125, 188 with the same peaks intensity relationship (FIG. 1A2).

It is likely that these ions are $NO_3^-$, $(HNO_3)\ NO_3^-$, and $(HNO_3)_2\ NO_3^-$ which formed as a result of oxidization (or solvating) of NO and $NO_2$ to $NO_3$ (or $HNO_3$). The humidity effect on the negative ion mass-spectra is smaller than on the positive ions. At elevated moisture conditions the major peaks are the same as for dry conditions m/z=62, 125, 188, but several new cluster peaks at significantly increased mass ($\Delta m=18$) also appeared (207, 225, 243, 261, etc.). From the mass spectra experiments it is obvious that water chemistry plays a very significant role in NOx ion formation, especially in the positive polarity. With increased moisture new cluster ions appear and as a result specific sample ion peak intensities decrease, due to the increased number of proton bounded water ions. (This may be an explanation for the suppression of conventional IMS response.)

According table I the photoionization source could not directly provide ionization of water molecules. A mechanism to explain formation of proton bounded water ions may be described by the following sequence of gas phase reactions:

$$W_{n-1}NO^+ + W + M \rightarrow W_n NO^+ + M, \quad (3)$$

where M is a non-reacting molecule, generally $N_2$.

When the water cluster around the $NO^+$ is sufficiently large, its proton affinity becomes sufficient for reaction to become exothermic. Theoretical calculations show that this occurs for n=3, i.e. $W_3NO^+$ is the critical size for the switch from $NO^+$ chemistry to protonated water chemistry.

$$W_3NO^+ + W \rightarrow HNO_2 + W_3H^+ \quad (4)$$

The peak at m/z 102 in the NOx mass-spectra 2 may be explained by this mechanism and may be the $W_4NO^+$ ion.

Evaluation of Memory Effects on Measurement Precision and Accuracy

In practice of the invention, memory effects were not a significant problem even though most characterization work was performed at room temperature. Furthermore, in real-world application, the gas temperature will be at least 100C, which will reduce or eliminate any memory effects should they occur.

Based upon the foregoing, it will be understood that we have shown highlights of the preferred practice of the present invention. Some of the highlights in practice of an illustrative embodiment of the invention include: NO samples are shown to produce a spectra containing only positive ion peaks. As expected there are no negative ions produced. $NO_2$ samples produce spectra containing a number of low intensity peaks in the positive mode (including a peak with the same compensation voltage as observed with the pure NO sample) and one major peak in the negative polarity mode. The NO spectra, even at room temperature in the presence of oxygen, is transformed into a spectrum representative of the $NO_2$ sample. Concentration dependence of NO and $NO_2$ samples have different approximations: NO has linear and $NO_2$ has quadratic approximation.

The estimated limit of detection for both species is around 1 ppm. Even in the presence of interferants, the negative ion spectra is stable and provides sufficient accuracy for NOx monitoring under real world conditions.

Mass spectrometric analysis of the positive and negative DMS spectra show that positive mode DMS peaks are mostly related to derivatives of $NO^+$ and protonated water ions. In the negative mode, the DMS peak contains ions of $NO_3^-$ and its derivatives, which are oxidation products of NO and $NO_2$. The formation of ions observed in the mass spectra are consistent with known chemistry but it must be emphasized that the systems are complex and there may be different channels (pathways) of ions formation which can explain obtained DMS/MS spectra.

It will now be appreciated that the present invention provides direct measurement of NOx, including NO and $NO_2$. High spectrometer sensitivity and ability to resolve NOx samples in real-time, even those not separated in conventional TOF-IMS, has been demonstrated. Further applications include an all-in-one detector that can make measurement of both hydrocarbon and NOx content in a gas sample in real-time. Thus such embodiment enables the realization of fast, miniature, low cost, high sensitivity, high reliability chemical detectors for detection of NOx and even of hydrocarbons in a gas sample, simultaneously.

Furthermore, the present invention enables a compact system for other detection needs, such as detection of NO in exhaled breath for monitoring and treatment of medical conditions. The present invention therefore has applications to these and other medical treatments as will be apparent to a person skilled in the art.

Therefore it will now be understood that the present invention discloses improved method and apparatus for gas sample analysis. Apparatus of the invention may feature planar, cylindrical, radial, or other DMS topologies and configurations. A preferred DMS embodiment of the invention enables a practical, small, fast (<100 msec), non-radioactive, sensitive and selective detector for real time monitoring of NOx.

The examples and embodiments disclosed herein are shown by way of illustration and not by way of limitation. The scope of these and other embodiments is limited only as set forth in the following claims.

What is claimed is:

1. System for chemical analysis of a gas sample, comprising:
   a flow path,
   a soft ionization source,
   an ion filter including ion filter electrodes across said flow path,
   an electronic input, said electronic input coupled to said ion filter electrodes for generating a high-low varying asymmetric displacement field between said electrodes across said flow path, said asymmetric displacement field imparting transverse motion to said flow of ion species according to mobility characteristics of said ion species and according to extant field conditions, said transverse motion driving unwanted ion species in said flow of ion species into said ion filter electrodes for neutralization thereof, said asymmetric displacement field being compensated, said compensation for selecting at least one ion species out of said flow of ion species and accommodating travel of said selected ion species in said flow path to said ion outlet for detection without said neutralization, said ion filter distinguishing between ion species of an ionized NOx sample based on differences in ion mobility in said filter field, and said filter passing selected said ion species of said ionized NOx sample for detection based on said compensation, and said detected, passed, selected, ion species being identified based on historical detection data of said system and on said extant field conditions.

2. System of claim 1 wherein said detected ion species is derived from an anthropogenic source of NOx.

3. System of claim 1 wherein said detected ion species is derived from an in vivo source of NO.

4. System of claim 1 wherein said detected ion species is NO and said system quantifies said detection.

5. System of claim 1 wherein said constituents of NOx include NO2, N2O4, and HN03.

6. System of claim 1 wherein NO is detected in a positive detection mode.

7. System of claim 1 wherein $NO_2$ is detected in a negative detection mode.

8. System of claim 1 wherein total NOx is detected by oxidation of said sample.

9. System of claim 1 wherein said means for ionizing said NOx sample is non-radioactive.

10. System of claim 9 wherein said means for ionizing said NOx sample is photon-based.

11. System of claim 1 wherein said detected ion species is quantified and identified based on historical detection data of said system and on said extant field conditions.

12. System of claim 1 wherein said detector simultaneously makes negative and positive mode detections of NOx components in a gas sample.

13. System of claim 1 wherein said detector simultaneously makes detections of NOx and hydrocarbon components in a gas sample.

14. System of claim 1 further including a combustor for the burning of fuel and controlled by a combustion controller, wherein effluent exhaust from said combustor is evaluated by said system and wherein detection of NOx is reported from said electronic part to said combustion controller to regulate said burning.

15. System of claim 1 further including a breath capture device for delivery of exhaled breath from a patient to said inlet part, wherein said breath is evaluated by said system and wherein detection of NO is reported from said electronic part to indicate the health of said patient.

* * * * *